US00PP37214P2

(12) United States Plant Patent
Hansen

(10) Patent No.: US PP37,214 P2
(45) Date of Patent: Jan. 13, 2026

(54) ***DIANTHUS* PLANT NAMED 'Whipped Cream'**

(50) Latin Name: ***Dianthus* hybrid**
Varietal Denomination: Whipped Cream

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,571

(22) Filed: Apr. 25, 2025

(51) Int. Cl.
*A01H 5/02* (2018.01)
*A01H 6/30* (2018.01)

(52) U.S. Cl.
USPC ..... Plt./274

(58) Field of Classification Search
USPC ..... Plt./274
CPC . A01H 5/02; A01H 5/00; A01H 6/305; A01H 6/30
See application file for complete search history.

(56) References Cited

U.S. PATENT DOCUMENTS

PP23,894 P2 * 9/2013 Bourne ..... A01H 6/305 Plt./279

OTHER PUBLICATIONS

Heritage Perennials Dianthus Everlast White + Eye, retrieved on Aug. 12, 2025 at https://www.perennials.com/plants/dianthus-everlast-white-eye.html, one page. (Year: 2025).*

* cited by examiner

*Primary Examiner* — June Hwu

(57) ABSTRACT

A new and unique plant cultivar of perennial carnation or pinks, *Dianthus* plant named 'Whipped Cream', with numerous highly-branched stems producing double, lightly-sweet fragrant flowers producing a full rounded face. Each flower has about twenty-two overlapping petals that are pure white with a small light-pink bar. Petals have finely dentate to crenate apices and margins. Flowering season is strong beginning in late spring and continues less densely to early-fall. The habit is compact and dense with glaucous silver-blue foliage.

1 Drawing Sheet

Botanical denomination: *Dianthus* hybrid.
Cultivar designation: 'Whipped Cream'.

STATEMENT REGARDING PRIOR DISCLOSURES UNDER 37 CFR 1.77(B)(6)

The first offering of the new plant was on May 20, 2024, by Walters Gardens, Inc. to Dallas Johnson Greenhouse, Inc. On Dec. 1, 2024, the new plant was first listed on websites for Proven Winners Direct™ in the form of photographs and a brief description. Proven Winners Direct™ and Walters Gardens, Inc. both obtained the plant and all information relating thereto, from the inventor. No plants of *Dianthus* 'Whipped Cream' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of carnation or pinks from the genus *Dianthus* and given the cultivar name 'Whipped Cream'. The new plant was the result of an intentional cross on Mar. 9, 2022, at a wholesale perennial nursery in Zeeland, Michigan, under the direction of the inventor between 'Sweetie Pie' U.S. Plant Pat. No. 27,989 as the female or seed parent and the male or pollen parent is 'WP15 MOW08' U.S. Plant Pat. No. 29,480.

The seed was harvested in May of 2022, and sown in the spring of 2022 and the new hybrid was first selected from trials at the same wholesale perennial nursery during the summer of 2023 as a single seedling clone and given the breeder code number 22-7-1 later in the evaluation processes.

*Dianthus* 'Whipped Cream' has been asexually propagated at the same nursery in Zeeland, MI since 2023 using traditional shoot tip cutting procedures and later sterile shoot-tip tissue culture and found to reproduce plants that are identical and exhibit all the characteristics of the original plant in successive generations.

SUMMARY OF THE INVENTION

*Dianthus* 'Whipped Cream' has not been evaluated under all possible environmental conditions. The phenotype may vary with variations in the environment including growing temperature, available sunlight, nutrition, water, etc. without a change in the genotype of the plant.

The closest comparison plants to the new plant known to the inventor include: 'KLEDG10116' U.S. Plant Pat. No. 23,363, 'WP10 VEN06' U.S. Plant Pat. No. 23,894, 'WP11 GWE04' U.S. Plant Pat. No. 25,027, and 'Aqua' (not patented).

'KLEDG10116' has a slightly taller habit and the flowers are slightly smaller with fewer petals that have more dissected margins and more magenta-pink, to the petal base. 'WP10VEN06' has a smaller habit and foliage, and the flowers have double pure white petals with more indented margins. 'WP11 GWE04' has flowers that lack the pink bar, the flower is much larger with more petals and petaloids, and the habit is much taller. 'Aqua' has a slightly taller habit, the flower petals are pure white and have a more deeply dentate apical margin.

The female parent, 'Sweetie Pie', has a taller habit with larger flowers, pink petals and slightly deeper pinkish eye and moderately dissected petal margins. The male parent, 'WP15 MOW08', has a taller habit, and the flowers are larger with more petals deeply serrate and are white and deep pink striped and speckled.

*Dianthus* 'Whipped Cream' is distinct from its parents and all other *Dianthus* known to the applicant in the following combined traits:

1. Double flowers with multiple overlapping petals forming a full domed face;
2. Petals have finely dentate to crenate apices;
3. Petal color is pure white with a small light pink bar;
4. Numerous flowers per plant on heavily branched upright stems;
5. Prolonged flowering period with a strong flush in late spring and continuing to early-fall;
6. Compact habit and dense, glaucous, silver-blue foliage.

BRIEF DESCRIPTION OF THE DRAWINGS

The photographs of 'Whipped Cream' are of a two-year-old plant grown in full-sun trial garden in Zeeland, Michigan showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
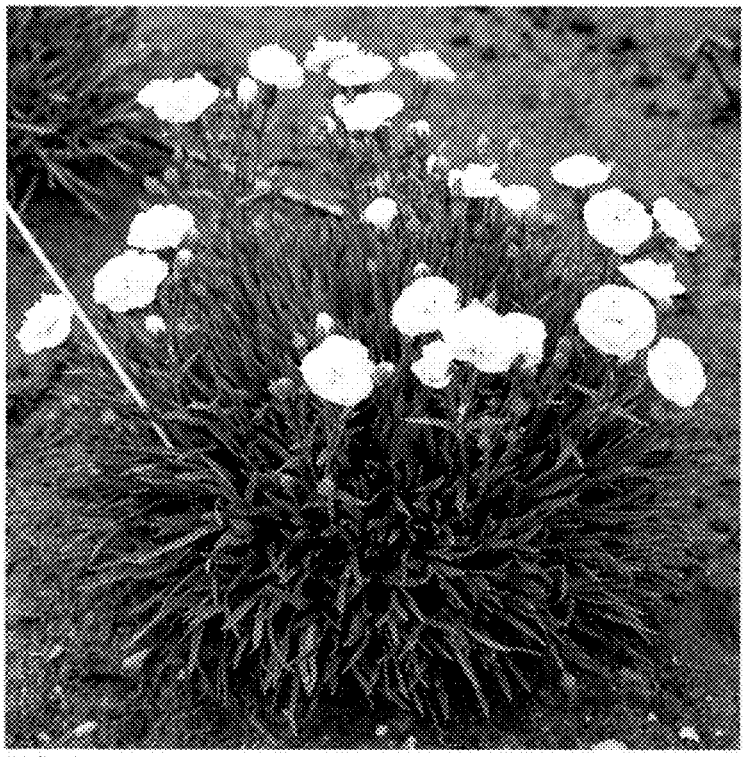
FIG. 1 shows the habit of the new plant in early-season flowering.
Figure 2:
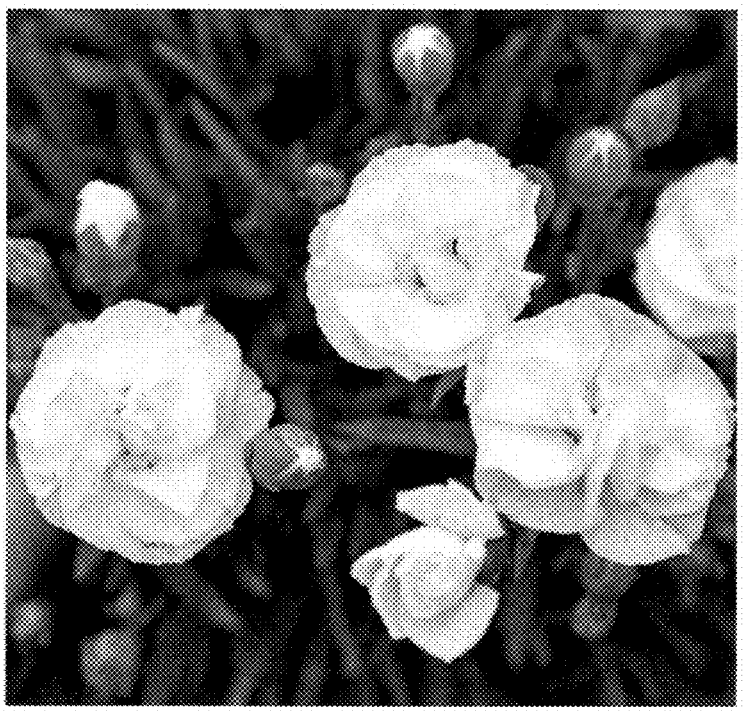
FIG. 2 shows a close-up of the flowers and buds.

The following detailed description of 'Whipped Cream' is based on observations of two- year-old plants in a full-sun trial garden at a nursery in Zeeland, MI with supplemental watering, light additions of fertilizer, and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 'Sweetie Pie'; the male or pollen parent is 'WP15 MOW08';

Plant habit: Caespitose, herbaceous, evergreen, winter-hardy perennial; stems and peduncles highly branched, mostly erect stems to slightly arching; height of foliage about 11 cm and about 24 cm across; height in flower is about 20 cm;

*Root system*.—Fine, fibrous; color nearest RHS 155D depending on soil substrate and nutrition.

*Vigor*.—Moderately vigorous; spring planted plugs finish in 3.8-liter pots in eight to ten weeks.

Foliage:

*Leaf type*.—Simple; linear; opposite; decussate; sessile; glabrous; glaucous both adaxial and abaxial; margin entire; apex narrowly acute; base truncate, decurrent, clasping; straight; very weakly concave; no fragrance detected; glaucosity medium.

*Leaf dimensions*.—To about 72 mm long and about 4 mm wide near middle, average about 50 cm long and 3.5 mm wide.

*Leaf color*.—Young expanding adaxial base nearest RHS 145C and distally nearest RHS 146B, abaxial base nearest RHS 145C and distally nearest RHS 146B; mature adaxial base nearest RHS 145D and distally between RHS N138A and RHS N138B, abaxial base nearest RHS 145C and distally between RHS N138A and RHS 189A.

*Venation*.—Not pronounced; obscurely pinnate, coloration same as that of adaxial and abaxial foliage.

Stems: About 150 per plant; upright; cylindrical, not fistulous; glabrous; glaucous; branching in upper nodes; center pithy;

*Stem size*.—About 13 cm long to peduncle and about 2.5 mm wide at base.

*Stem color*.—Between RHS N138A and RHS N138B.

*Branching*.—Numerous; typically alternate from lower nodes; about 12 per main stem and about 300 per plant in late spring peak; branch size average to about 5 cm long and 1 mm diameter at time of initial flowering.

*Nodes*.—About 5 mm across; color nearest RHS 145C.

*Internodes*.—About 10 to 12 per stem before peduncle; average about 5 mm apart depending on growing temperature, shorter in cooler conditions.

Inflorescence: Flowering in the upper 8 cm and to about 6.5 cm across; heavily branched with about 3 to 6 flowers per inflorescence;

*Flower bud*.—With calyx still closed and petals style contain within calyx: slowly opening; glabrous; glaucous; cylindrical with attenuate base and acute apex; about 28 mm long and 8 mm across.

*Flower bud color*.—Nearest RHS NN155D.

Flower:

*Type*.—Terminal, cymose; perfect; salverform; actinomorphic; double.

*Attitude*.—Upright to slightly outwardly around perimeter of plant.

*Dimension*.—About 2.7 cm across and extending about 3.0 cm above base of calyx tube, calyx tube to about 1.7 cm tall and 9 mm wide at apex of calyx.

*Flowers per stem*.—Up to 14, average 12; with two to four inflorescences per stem.

*Pedicel*.—Glaucous, glabrous, cylindrical, stiff; primarily upright.

*Pedicel size*.—To about 2.2 cm long and about 2 mm diameter.

*Pedicel color*.—Between N138A and RHS N189C.

*Flower period*.—Beginning in late May with a strong flush for about four weeks and continuing more sparsely through mid-fall.

*Flower fragrance*.—Sweet, spicy, clove-like.

*Flower lasting quality*.—Individually about seven to ten days on or cut from plant.

*Corolla profile*.—Dome-shaped.

*Petals*.—About 22; glabrous adaxial and abaxial except at proximal half of adaxial limb puberulent; consisting of a limb and a claw; limb obdeltoid, and limb and claw combined are flabellate; limb apex and margin finely dentate to crenate, with teeth to about 1 mm long and 1 mm wide at base, and many small incisions per petal margin; limb base attenuate toward claw; claw with attenuate base; bent outwardly at limb base creating a flat rounded face; persistent; having a lighter eye.

*Petal dimensions*.—Limb to about 12 mm long and 17 mm wide; claw about 15 mm long and 6 mm wide tapering to attenuate base of about 0.5 mm across; whole petal to about 28 mm long, average about 26 mm long; middle adaxial bar in a perpendicular bar on the veins about 0.5 mm wide and about 9 mm from apex.

*Petal color*.—Young adaxial and abaxial limb distal portion nearest NN155D; middle adaxial perpendicular bar nearest RHS 64B blushed stronger in cooler weather and not present in very warm condition; adaxial and abaxial proximal claw portion nearest RHS 155D, adaxial and abaxial center claw portion between RHS 145A and RHS 145B; adaxial and abaxial distal claw portion nearest RHS NN155D with darker perpendicular bar along the veins of nearest RHS 64A extending into the limb about 5 mm, claw nearest RHS 145C proximally with distal claw before limb nearest RHS NN155C; young abaxial limb nearest RHS 71C and transitioning to nearest RHS NN74D toward margin, claw nearest RHS 145C proximally with distal claw before limb nearest RHS NN155C; no change in color with maturity.

*Calyx*.—Tubular; nearly straight; to about 17 mm long and 9 mm diameter at apex.

*Sepals*.—Five; acute apex and fused in basal 13 mm forming five-toothed calyx tube; glabrous adaxial and abaxial; glaucous abaxial; margins entire.

*Sepal size*.—Individually about 17 mm long and about 5 mm across at fusion.

*Sepal color*.—Adaxial nearest RHS 147C; abaxial nearest RHS 138A; without anthocyanin in warmer conditions and with adaxial apex blushed with nearest RHS 183B in cooler conditions.

*Peduncle*.—Glabrous; glaucous; cylindrical, not fistulous; stiff; about 10 cm long and about 3 mm diameter at base; attitude mostly upright.

*Peduncle color*.—Blend nearest RHS N138B and RHS 189C with light glaucous bloom.

*Epicalyx*.—Two pairs subtending each calyx; both pairs adpressed; opposite; lightly glaucous, glabrous; sessile; margin entire; broadly ovate; inner pair narrowly acute apex, and truncate base, 8 mm long and about 8 mm across near middle; outer pair with very short narrowly acute apex, truncate clasping base, about 7 mm long and about 7 mm wide.

*Epicalyx color*.—Both pairs adaxial and abaxial translucent to transparent margin, proximal portions nearest RHS 146D, distal portions between RHS NN137A and RHS NN138A; no anthocyanin pigment observed.

*Androecium*.—Typically, 12. Filaments: straight, curving outwardly with maturity; 12 to 16 mm long and 0.5 mm diameter; color nearest RHS NN155B. Anther: oblong; basifixed; rudimentary; about 1 mm long and 0.5 mm across; color nearest RHS 161C. Pollen: not observed.

*Gynoecium*.—Single; to about 26 mm long. Style: bifurcate just above ovary; shoulder absent; to 10 mm long and 1 mm diameter; color nearest RHS NN155C, hairs nearest RHS NN155D. Stigma: linear; puberulent along adaxial surface; about 9 mm long and 0.5 mm wide; color nearest RHS NN155D. Ovary: superior; cylindrical; rounded apex and truncate base; smooth; lustrous; about 7 mm long and 4 mm diameter; color distal half nearest RHS 145A and proximal half nearest RHS 145C.

Fruit and seeds: Not observed under present growing conditions, but sterility is not confirmed;

Disease resistance: The new plant is resistance to center die out from fungus or high temperatures.

Growth: The plant grows best with adequate moisture and well-drained soil but tolerates some drought once established. Hardiness at least from USDA zone 4 through zone 9.

It is claimed:

1. A new and distinct *Dianthus* plant named 'Whipped Cream' essentially as herein described and illustrated.

* * * * *